United States Patent [19]

Harrison et al.

[11] Patent Number: 5,322,072

[45] Date of Patent: Jun. 21, 1994

[54] STERILITY MAINTENANCE COVER, SURGICAL INSTRUMENT TRAY, AND DRAPE SUPPORT

[76] Inventors: Samuel W. Harrison, 4003 Scenic Dr., Shreveport, La. 71119; Michelle L. Grabski, 423 Maple Ridge Dr., Bossier City, La. 71111

[21] Appl. No.: 47,269

[22] Filed: Apr. 14, 1993

[51] Int. Cl.$^5$ .................................................. A61B 19/00
[52] U.S. Cl. ........................................ 128/849; 128/857; 128/863; 5/507.1; 248/174
[58] Field of Search ............... 128/846, 849, 850, 851, 128/852, 853, 854, 855, 857, 858, 205.56, 863; 602/74; D6/485, 406; 108/92; 297/391; 248/174; D15/126; D29/6, 10, 16, 99

[56] References Cited

U.S. PATENT DOCUMENTS

| | | | |
|---|---|---|---|
| 3,889,670 | 6/1975 | Loveland et al. | 128/205.26 |
| 4,003,378 | 1/1977 | Pickering | 128/205.26 |
| 4,018,217 | 4/1977 | Evans | 128/849 |
| 4,275,719 | 6/1981 | Mayer | 128/849 |
| 4,936,318 | 6/1990 | Schoolman | 128/849 |
| 5,005,590 | 4/1991 | Eldridge, Jr. et al. | 128/849 |

OTHER PUBLICATIONS

*Interior*, p. 52, Dec., 1973, "A New Strauss Step".

*Primary Examiner*—Robert A. Hafer
*Assistant Examiner*—Michael O'Neill
*Attorney, Agent, or Firm*—John M. Harrison

[57] ABSTRACT

A device for maintaining sterility during which device includes an L-shaped member having a base panel for fitting beneath the patient, an upward-standing side or end panel and a horizontally oriented instrument platform extending from the side or end panel above the patient's head, neck and shoulders for receiving instruments during surgery. The device facilitates draping of the patient's head to insure a sterile operating field which is maintained throughout the surgical procedure. In a preferred embodiment, the instrument panel and the end or side panels may be removed from the base panel.

3 Claims, 1 Drawing Sheet

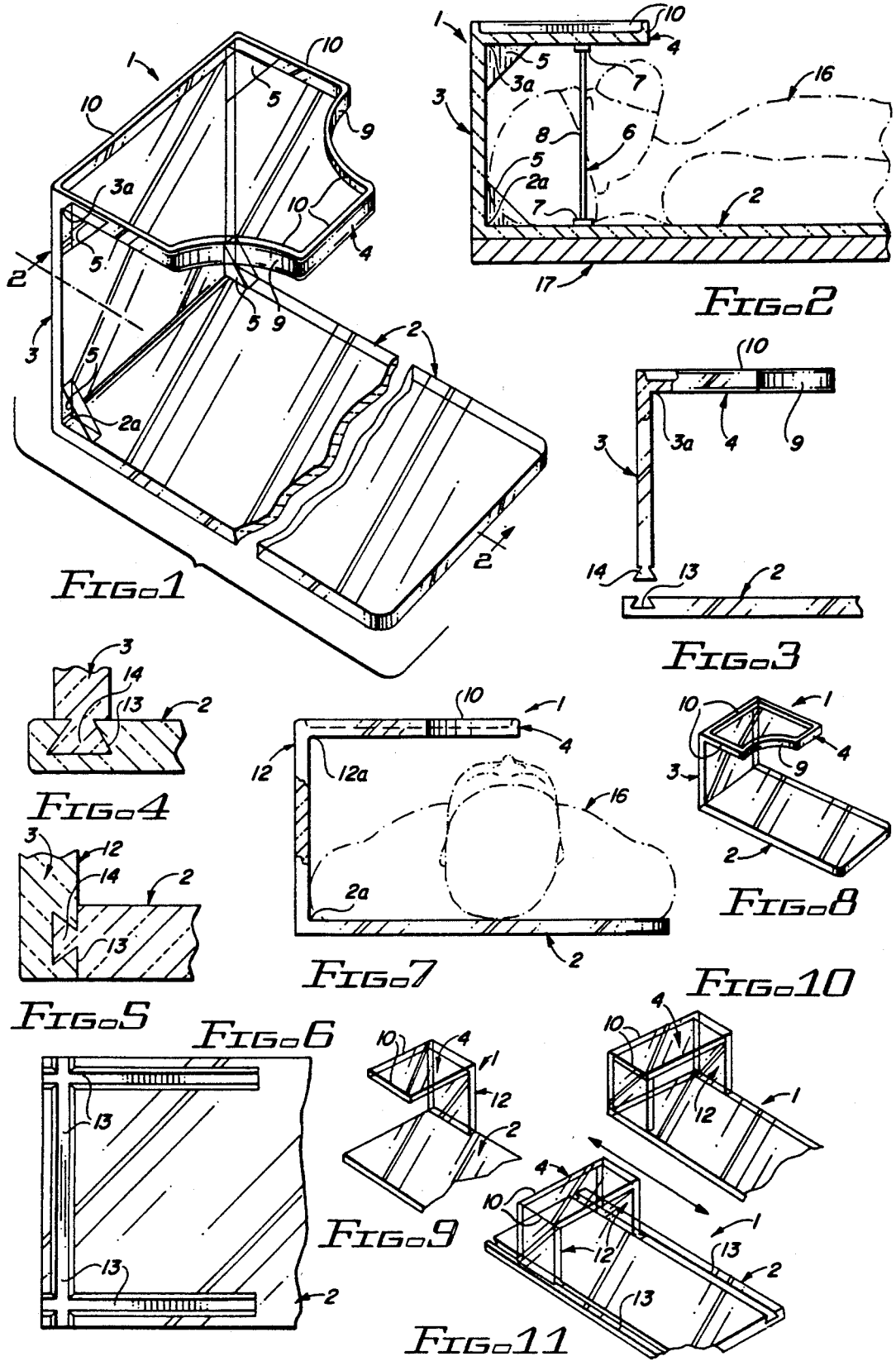

STERILITY MAINTENANCE COVER, SURGICAL INSTRUMENT TRAY, AND DRAPE SUPPORT

BACKGROUND OF THE INVENTION

1. Field of the Invention

During surgical procedures such as pacemaker implants and similar procedures, it is imperative that the patient's head be draped in a sterile manner to insure that a sterile field is maintained throughout the operation. Various methods have been employed to achieve this result, including various types of draping techniques, supports and devices. The sterility maintenance cover of this invention is designed for optimum effective results in achieving sterility during certain types of operating procedures. The apparatus includes an L-shaped transparent support having a base panel for fitting under the head, neck and shoulders of a patient, an upward-standing end or side panel or panels and an instrument panel projecting from the end or side panel horizontally, substantially parallel to the base panel over the patient's head and neck. The instrument panel is designed to receive and retain various instruments used in the surgical procedure and may be fitted with curved cutaways or scallops, to provide easy access to the patient and an upward-standing lip to maintain the instruments in position on the instrument platform. Various types of built-in or removable supports may also be utilized to maintain the instrument platform in substantially horizontal position, parallel to the base panel.

It is an object of this invention to provide a new and improved device for maintaining surgical sterility during surgical procedures in the head, shoulder and upper torso area.

Another object of the invention is to provide a new and improved sterility maintenance cover which is constructed of clear material and includes a base panel for fitting under the head, neck and shoulders of a patient, an upward-standing end or side panel and an instrument platform extending from the end or side panel substantially parallel to the base panel over the head and neck of the patient for receiving and containing instruments during the surgical procedure.

Yet another object of this invention is to provide a new and improved sterility maintenance cover for effecting surgical sterility in draping of a patient during certain surgical operations, which cover is characterized by an L-shaped, transparent, radioluscent device, the base panel of which fits under the head, neck and upper back of the patient and an end or side panel projecting fixedly or removably upwardly from the base panel, with an instrument platform extending from the end or side panel over the patient's head and neck to support surgical instruments and apparatus during the operation.

SUMMARY OF THE INVENTION

These and other objects of the invention are provided in a new and improved sterility maintenance cover for draping a patient in a sterilized manner during surgery, which instrument cover is characterized by a transparent, L-shaped polymeric device having a base panel for fitting on the operating table beneath the head, neck and shoulders of a patient, a transparent end or side panel projecting upwardly in fixed or removable relationship from the base panel and a transparent instrument panel extending from the end or side panel substantially parallel to the base panel and horizontally over the patient's head and neck, with scallops and a lip provided on the instrument platform receive and contain surgical and accessory instruments during operations.

BRIEF DESCRIPTION OF THE DRAWING

The invention will be better understood by reference to the accompanying drawing, wherein:

FIG. 1 is a perspective view of a preferred embodiment of the sterility maintenance cover of this invention;

FIG. 2 is a sectional view taken along line 2—2 of the sterility maintenance cover of this invention;

FIG. 3 is a side view of an alternative preferred embodiment of the sterility maintenance cover;

FIG. 4 is a sectional view of a tongue-and-groove joint in the sterility maintenance cover of FIG. 3;

FIG. 5 is an alternative tongue-and-groove joint;

FIG. 6 is yet another alternative tongue-and-groove joint;

FIG. 7 is an end view of the sterility maintenance cover illustrated in FIG. 1;

FIG. 8 is yet another alternative preferred embodiment of the invention;

FIG. 9 is still another alternative preferred embodiment of the invention;

FIG. 10 is yet another alternative preferred embodiment of the invention; and

FIG. 11 is still another alternative preferred embodiment of the invention.

DESCRIPTION OF THE PREFERRED EMBODIMENTS

Referring initially to FIGS. 1 and 2 of the drawing, in a preferred embodiment the sterility maintenance cover of this invention is generally illustrated by reference numeral 1. The sterility maintenance cover 1 is constructed of a transparent material such as "Plexiglass" (trademark) or "Lexan" (trademark) polymeric materials which are well known to those skilled in the art and includes a flat base panel 2 designed to lie flat on an operating table beneath the head, neck and shoulders of a patient, as illustrated. An end panel 3 projects upwardly from one end of the base panel 2 and an instrument platform 4 extends from the top edge of the end panel 3, substantially parallel to the base panel 2, over the head of the patient 16. One or more gussets 5 may be provided in the base panel bend 2a and end panel bend 3a at the base panel 2 and the end panel 3, as well as the instrument platform 4, to better support the instrument platform 4 in substantially parallel relationship with respect to the base panel 2, for purposes which will be hereinafter further described. Furthermore, as illustrated in FIG. 1 platform cutaway scallops 9 are provided in the instrument platform 4 to facilitate better access to the patient 16 lying beneath the instrument platform 4. Moreover, a platform lip 10 is provided around the periphery of the instrument platform 4 to contain various instruments (not illustrated) during a surgical procedure. Accordingly, it will be appreciated by those skilled in the art that the instrument platform 4 serves as an instrument tray for positioning various types of instruments and accessory items used in the operating procedure to facilitate close access of the instruments to the patient 16, nurse, anesthesiologist and surgeon. Furthermore, the transparency of the instrument platform 4 and the end panel 3 allows observation of the patient at all times by the anesthesiologist, as well as the surgeon and attending physicians and nurses.

Referring again to FIG. 2 of the drawings, in lieu of, or in addition to the gussets 5, a support 6 may be provided for extension between the instrument platform 4 and the base panel 2 to support the instrument platform 4 in the desired substantially horizontal position with respect to the base panel 2. The support 6 may typically include support ends 7 which are characterized by suction cups or other rubber or plastic tips mounted on both ends of a support rod 8 of selected length.

Referring now to FIGS. 7 and 9 of the drawings, it will be appreciated by those skilled in the art that the end panel 3 of the sterility maintenance cover 1 may be eliminated in favor of a side panel 12, which leaves the end portion of the sterility maintenance cover 1 open for quick and ready access by the anesthesiologist, who is normally located at the head of the patient during an operation or procedure. Accordingly, the instrument platform 4 extends from the top edge of the side panel 12 at a side panel bend 12a in the same manner as the instrument platform 4 projecting from the end panel 3 illustrated in FIG. 1. It will be further appreciated by those skilled in the art that although the side panel 12 illustrated in FIGS. 7 and 9 is located on the left-hand side of the sterility maintenance cover 1 for purposes of illustration, the side panel 12 may equally well be positioned on the right-hand side of the sterility maintenance cover 1, connecting the base panel 2 to the instrument panel platform 4, as desired. Moreover, transparent gussets 5 of selected size may be provided at the base panel bends 2a and side panel bend 12a, with or without a support 6, as illustrated in FIG. 2.

Referring to FIGS. 3-6 of the drawings, it is sometimes desirable to remove the end panel 3 and connected instrument panel 4 from the base panel 2, either before, during or after a procedure. Accordingly, one edge of the base panel 2 (FIGS. 4 and 6) or the end panel 3 (FIG. 5) is fitted with a dovetail panel slot 13, while the bottom edges of the end panel 3 (FIG. 4) and front edge of the base panel 2 (FIG. 5) are shaped to define a dovetail panel flange 14, which slidably engages the panel slots 13, respectively, to removably mount the instrument platform 4 and the end panel 3 on the base panel 2, as illustrated. It will be appreciated by those skilled in the art that the same combination of panel slot 13 and panel flange 14 may be utilized in the side panel 12 to disconnect the side panel 12 and instrument platform 4 from the base panel 2, as illustrated in FIG. 6. Other variations of the sterility maintenance cover 1 are illustrated in FIGS. 8-11.

It will be further appreciated by those skilled in the art that the sterility maintenance cover of this invention facilitates quick and easy draping of a patient for various types of operations, including pacemaker implants, heart catherization procedures and the like. Because the end panel 3 or side panel(s) 12 and the instrument platform 4 are transparent, the patient may be viewed at all times during the operation by the anesthesiologist, cardiologist or surgeon and the other attending physicians and nurses, as desired. Moreover, the sterility maintenance cover 1 can be designed to utilize an end panel 3 or one or more side panel(s) 12, as described above, depending upon the particular type of access desired to the patient. In a most preferred embodiment a polymeric material such as "Plexiglass" or "Lexan" in nonexclusive particular, of sufficient thickness can be utilized to provide the necessary structural integrity, such that the sterility maintenance cover may be manufactured from a single piece of material wherein the base panel 2, end panel 3, or side panel(s) 12 and the instrument panel 4 are shaped at the base panel bend 2, end panel bend 3 or side panel bend 12a, according to techniques which are well known to those skilled in the art. Alternatively, as described above, the base panel 2, end panel 3 and/or side panel(s) 12 may be fitted with a dovetail or similar panel slot 13, while a corresponding panel flange 14 is provided in either the end panel 3 or the side panel(s) 12 for slidable engagement with the panel slot 13, to facilitate removing the instrument platform 4 and the end panel 3 or side panel(s) 12 from the base panel 2.

While the preferred embodiments of the invention have been described above, it will be recognized and understood that various modifications may be made in the invention and the appended claims are intended to cover all such modifications which may fall within the spirit and scope of the invention.

Having described my invention with the particularity set forth above, what is claimed is:

1. A device for maintaining sterility of a patient lying on an operating table comprising a base panel for insertion between the head, neck and shoulders of the patient and the operating table; a transparent support panel extending upwardly from one end of said base panel; a transparent instrument platform extending from one end of said support panel over at least the head of the patient and having two sides and a free end for supporting medical instruments; a pair of cutaways extending from said side of said instrument platform to said free end of said instrument platform for accessing said patient; and a lip upward-turned from the periphery of said instrument platform and said cutaways for containing the medical instruments.

2. The device of claim 1 wherein said support panel comprises an end panel.

3. The device of claim 1 wherein said support panel comprises a side panel.

* * * * *